United States Patent [19]

Seifert et al.

[11] 4,045,496
[45] Aug. 30, 1977

[54] PROCESS FOR THE HYDROXYLATION OF PHENOLS AND PHENOL ETHERS IN THE NUCLEUS

[75] Inventors: Hermann Seifert, Cologne; Helmut Waldmann; Wulf Schwerdtel, both of Leverkusen; Wolfgang Swodenk, Odenthal-Gloebusch, all of Germany

[73] Assignee: Bayer Aktiengesellschaft, Leverkusen, Germany

[21] Appl. No.: 553,939

[22] Filed: Feb. 28, 1975

[30] Foreign Application Priority Data

Mar. 6, 1974 Germany .............................. 2410758

[51] Int. Cl.² ............................................. C07C 37/00
[52] U.S. Cl. ............................ 260/613 D; 260/621 G; 260/625; 260/623 R; 260/622 R; 260/473 S; 260/619 D; 260/620; 260/619 F; 260/613 R

[58] Field of Search .......... 260/621 G, 613 D, 622 R, 260/625, 613 R, 619 F, 619 D, 623 R, 473 S, 620

[56] References Cited

U.S. PATENT DOCUMENTS

| 3,549,709 | 12/1970 | Achard et al. ............. 260/613 D X |
|---|---|---|
| 3,836,591 | 9/1974 | Maggioni ..................... 260/621 G |
| 3,849,502 | 11/1974 | Bourdin et al. ............ 260/613 D X |

Primary Examiner—Bernard Helfin
Attorney, Agent, or Firm—Burgess, Dinklage & Sprung

[57] ABSTRACT

A process for the hydroxylation of phenols and phenol ethers in the nucleus with hydrogen peroxide wherein a phenol or a phenol ether is reacted at the start of the reaction with substantially anhydrous hydrogen peroxide and wherein the reaction is carried out in the presence of a strong acid.

20 Claims, No Drawings

PROCESS FOR THE HYDROXYLATION OF PHENOLS AND PHENOL ETHERS IN THE NUCLEUS

This invention relates to a process for the hydroxylation of phenols and phenol ethers in the nucleus with hydrogen peroxide.

It is known that phenols and phenol ethers can be hydroxylated in the nucleus with aqueous hydrogen peroxide in the presence of catalytic quantities of a strong acid German Auslegeschrift No. 2,064,497). The initial concentration of water in the reaction mixture, which is not regarded as critical, is less than 20% and preferably less than 10%. According to German Auslegeschrift No. 2,064,497, yields of around 70% of a hydroxylated product, based on the hydrogen peroxide used, are obtained by using a 20-fold molar excess of a phenol, based on the quantity of peroxide, and working with hydrogen peroxide with a water content of about 5% (Example 1 of German Auslegeschrift No. 2,064,497). In cases where hydrogen peroxide with a water content of 56% is used, the yield of hydroxylated product is reduced to 63% under the same reaction conditions, whilst the reaction time is increased from 30 minutes to 3 hours (Example 3 of German Auslegeschrift No. 2,064,497). According to German Auslegeschrift No. 2,064,497, a reduction in the excess of phenol from 20 mols to 10 mols, based on 1 mol of hydrogen peroxide, reduces the yield to 60 % under otherwise the same reaction conditions (Example 7 of German Auslegeschrift No. 2,064,497).

The use of high concentrations of hydrogen peroxide involves the danger of explosions and, for this reason, necessitates elaborate and expansive safety precautions where a process is intended for working on a commercial scale. According to Winnacker-Juchler, Chemische Technologie, Vol. 1, page 561 (1969), the concentration limit at which aqueous hydrogen peroxide solutions are capable of being detonated is 90%. Since the presence of organic compounds reduces the concentration limit to 70% (R. Powell "Hydrogen Peroxide Manufacture," page 184 (1968)), the working conditions of German Auslegeschrift No. 2,064,497 always involve the danger of explosions.

According to German Pat. No. 1,543,830, this difficulty can be obviated by carrying out the hydroxylation of aromatic compounds in the nucleus with hydrogen peroxide in the presence of boric acid or a boric acid derivative, and subsequently hydrolysing the resulting boric acid esters of the hydroxylated aromatic compounds, the hydrogen peroxide being introduced into the reaction in the form of a dilute, non-aqueous solution. One of the disadvantages of using boric acid derivatives is that the boric acid derivatives of the required products are initially formed from the aromatic compounds to be hydroxylated and have to be subsequently hydrolysed in a following process stage.

A process for hydroxylating phenols and phenol ethers in the nucleus with hydrogen peroxide in the presence of a strong acid has now been found, which is characterised by the fact that, at the beginning of the reaction, hydroxylation is carried out with substantially anhydrous hydrogen peroxide.

Compounds which may be hydroxylated by the process according to the invention are, for example, phenols and phenol ethers which consist of up to 3 condensed benzene nuclei and which contain at least 1 free hydrogen atom in the benzene nucleus. The phenols and phenol ethers may optionally carry nitro, cyano, chlorine, fluorine, carbo-$C_1$-$c_3$-alkoxy, $C_1$-$C_6$-alkyl, $C_5$-$C_7$-cycloalkyl or phenyl groups on the nucleus.

The hydrogen atom of the phenolic hydroxyl group of the phenols upon which the phenol ethers are based may be substituted by, for example, an alkyl radical, for example, methyl, ethyl, propyl, isopropyl, cyclohexyl, butyl, isobutyl, tert.-butyl, preferably methyl, ethyl, isopropyl or an aryl radical, for example phenyl, naphthyl, preferably phenyl. The following are mentioned as examples of compounds which may be used for the process according to the invention: p-nitrophenol, o-nitrophenol, m-nitrophenol, p-chlorophenol, o-chlorophenol, m-chlorophenol, p-carbomethoxy phenol, o-cresol, m-cresol, p-cresol, p-cyclohexyl phenol, o-cyclohexyl phenol, p-phenyl phenol, o-phenyl phenol, m-phenyl phenol, p-ethyl phenol, o-ethyl phenol, m-ethyl phenol, p-isopropyl phenol, p-tert.-butyl phenol, anisole, p-nitroanisole, p-chloroanisole, o-chloroanisole, m-chloroanisole, p-methyl anisole, o-methyl anisole, m-methyl anisole, p-phenyl anisole, phenyl ethyl ether, phenyl isopropyl ether, p-methyl phenyl isopropyl ether, $\alpha$-naphthol, $\beta$-naphthol, $\alpha$-methoxy naphthalene, neroline, 1-hydroxy-4-methyl naphthalene, 1-hydroxy-2-methyl naphthalene, 2-hydroxy-1-methyl naphthalene, 2-hydroxy-6-methyl naphthalene, 1-hydroxy-4-isopropyl naphthalene, 1-hydroxy-4-t-butyl naphthalene, 1-hydroxy-6-phenyl naphthalene, 1-hydroxy-6-methoxy naphthalene, 1-isopropyl naphthalene, 2-isopropoxy naphthalene, 1-phenyloxy naphthalene, 2-phenyloxy naphthalene, 1-hydroxy anthracene, 1-methoxy anthracene, 2-hydroxy anthracene, 2-methoxy anthracene, 3-hydroxy phenanthrene, 1-hydroxy phenanthrene, 9-methoxy phenanthrene, 1-methoxy phenanthrene and 3-methoxy phenanthrene.

It is preferred to use phenols and phenol ethers with substituents which direct the new hydroxyl group into the ortho- or para-position.

The following are mentioned as examples of compounds of this kind: o-chlorophenol, p-chlorophenol, o-cresol, m-cresol, p-cresol, p-cyclohexyl phenol, o-cyclohexyl phenol, p-ethyl phenol, o-ethyl phenol, anisole, o-chloroanisole, p-chloroanisole, o-methyl anisole, phenyl isopropyl ether, phenyl ethyl ether, o-phenyl phenol, 4-tert.-butyl phenol and p-phenyl phenol.

It is particularly preferred to use o-cresol, m-cresol, p-cresol, anisole, 4-tert.-butyl phenol and p-phenyl phenol.

The phenols and phenol ethers used for the process according to the invention should have as low a water content as possible. It is possible to use commercial-grade phenols and phenol ethers which should contain no more than 0.1% of water.

Thus, according to the present invention, the hydrogen peroxide used for the process is in the form of a substantially anhydrous solution. The concentration of the hydrogen peroxide in the solvent may be adjusted so that there is no danger of explosion.

The hydrogen peroxide used for the process according to the invention may be dissolved in an further anhydrous solvent. Examples of suitable solvents include aliphatic ethers or alkyl esters such as diethyl ether, diisopropyl ether, diisoamyl ether, isoamyl acetate, preferably isoamyl acetate.

These solutions contain up to 6% of hydrogen peroxide.

Solvents which allow a higher concentration of hydrogen peroxide are the esters and N-alkyl amides of phosphoric acid, phosphonic acid and phosphinic acid, for example tri-n-propyl phosphate, tri-n-butyl phosphate, triisooctyl phosphate, hexamethyl phosphoric acid triamide, methanophosphonic acid dimethyl ester, β-carbomethoxy ethanophosphonic acid methyl ester and methanophosphonic acid tetramethyl amide; the preferred phosphororganic solvents being methanophosphonic acid dimethyl ester and trisooctyl phosphate.

One particularly suitable solvent for anhydrous hydrogen peroxide solutions is N-methyl pyrrolidone, in which up to 30% of the hydrogen peroxide is dissolved.

It is particularly advantageous and simple to use an anhydrous solution of hydrogen peroxide in the material to be hydroxylated in the process according to the invention.

In one preferred embodiment, an anhydrous solution of hydrogen peroxide in phenols or phenol ethers is prepared, for example, by extractive distillation. To this end, the phenol or the phenol ether which is to be hydroxylated by the process according to the invention is initially introduced into a distillation column, followed by the addition of aqueous hydrogen peroxide in a concentration of from 10% to 50%, preferably 15%, at a rate commensurate with that at which water is distilled off overhead, preferably in a vacuum of 10 to 100 Torr. An anhydrous solution of hydrogen peroxide in the phenol or the phenol ether is obtained as residue in the distillation column.

It is also particularly advantageous and simple to prepare anhydrous solutions of hydrogen peroxide in phenols or in phenol ethers by distilling off the hydrogen peroxide and the phenol or the phenol ether together from an anhydrous solvent having a boiling point higher than that of the phenol or phenol ether and the hydrogen peroxide. Basically, any organic solvents which are chemically inert under the reaction conditions and which boil at higher temperatures than the phenol or phenol ether and the hydrogen peroxide, are suitable for use as nonaqueous solvents for hydrogen peroxide in this advantageous embodiment of the process according to the invention. It is of advantage for the difference in boiling point between the reactants and the solvent to amount to 50° C. Examples of suitable solvents are tri-n-butyl phosphate, tri-n-octyl phosphate, tri-[(2-ethyl)-hexyl]-phosphate, hexamethyl phosphoric acid triamide, β-carbomethoxy ethanophosphonic acid methyl ester, β-carbohydroxy ethanophosphonic acid methyl ester. It is preferred to use triisooctyl phosphate and tributyl phosphate.

A 5 to 30% solution and preferably a 10 to 25% solution of hydrogen peroxide in an anhydrous organic solvent is used for the advantageous embodiment of the process according to the invention described above.

To prepare the anhydrous hydrogen peroxide solution in the phenol intended for hydroxylation by common distillation from the higher boiling solvent, the phenol or the phenol ether and the non-aqueous hydrogen peroxide solution may be mixed, the order in which the components are added during mixing being basically of an arbitrary nature. However, it is preferred to introduce vapours of the phenol or phenol ether to be hydroxylated into the non-aqueous solution of hydrogen peroxide in an inert, higher boiling solvent and to react the vapour mixture of phenol or phenol ether and hydrogen peroxide which distils over before or after condensation by means of a catalytic quantity of a strong acid. The common distillation of hydrogen peroxide and phenol or phenol ether is with advantage carried out in a distillation apparatus equipped with a sump receiver, column, condenser and reflux divider. It is particularly advisable to introduce the hydrogen peroxide solution near the head of the column and the phenol or the phenol ether near the sump of the column, so that optimum charging of the vapours with hydrogen peroxide on the one hand, and optimum evaporation of the hydrogen peroxide from the solvent on the other hand, are obtained in accordance with the countercurrent principle.

On account of the thermal instability of hydrogen peroxide, the pressure prevailing in the distillation apparatus during the distillation of hydrogen peroxide with phenols or phenol ethers is best selected so that the temperature of the distillation sump is between 100° C and 20° C and preferably between 80° C and 50° C. The vacuum required for this purpose is generally in the range from 0.1 to 500 Torr and preferably in the range from 5 to 200 Torr. The vapours distilling over, which consist of phenol or phenol ether and hydrogen peroxide, generally have hydrogen peroxide concentrations of from 0.5 to 15%. It is particularly simple by this process to prepare an approximately 15% anhydrous solution of hydrogen peroxide in phenol. Solutions of hydrogen peroxide in phenol are not explosive and are easy to handle in this concentration range. By suitably selecting the quantitative ratios, the recycle ratio prevailing during distillation and, above all, the hydrogen peroxide concentration of the starting solution, it is possible to prepare solutions of hydrogen peroxide in phenols or phenol ethers with as low a concentration as required.

Since phenols or phenol ethers are used in a large excess for the process according to the invention, it is possible to adjust hydrogen peroxide concentrations of from 0.5 to 4% and preferably from 2.5 to 3.0% in the phenol or phenol ether. The phenols or phenol ethers are used in an excess of from 3 to 20 mols, preferably from 10 to 15 mols, per mol of hydrogen peroxide.

Any strong acids which are inert under the reaction conditions may be used as the acids with which hydroxylation of the phenol or phenol ether is catalysed. It is possible for example to use sulphuric acid, sulphuric acid in admixture with phosphoric acid, perchloric acid, nitric acid, trifluoromethane sulphonic acid, perfluorobutane sulphonic acid, fluorinate acid ion exchangers of the sulphonated polymeric fluorine-substituted hydrocarbon type, fluorosulphonic acid or fluorosulphonic acid in admixture with antimony pentafluoride.

The quantity of strong acid may vary within wide limits. The acid is generally used in a quantity of from 0.01 to 2 mols and preferably in a quantity of from 0.1 to 1.5 mols per mol of hydrogen peroxide.

It is known that, in reactions with hydrogen peroxide, decomposition catalysts may either be excluded or inactivated by suitable complex formers. Examples of decomposition catalysts for hydrogen peroxide include copper, cobalt, vanadium, manganese, chromium and iron salts. As already known, suitable complex formers are phosphates or partially esterified acids of phosphorus. The neutral esters or the N-alkyl amides of phosphoric acid, phosphonic acid and phosphinic acid are particularly suitable, so that there is no need for additional stabilisation in cases where hydrogen peroxide is used in esters or alkyl amides of phosphoric acid, phosphonic acid or phosphinic acid for the hydroxylation of phenols or phenol ethers in accordance with the invention. Where other solvents for hydrogen peroxide or solutions of hydrogen peroxide in the phenol or phenol ether to be hydroxylated are used, it is best to add stabilisers, preferably esters or N-alkyl amides of phosphoric acid. Examples of suitable stabilisers are methanophosphonic acid esters, triisooctyl phosphate, β-carbomethoxy methanophosphonate, hexamethyl phosphoric acid triamide.

The quantity of stabilisers may vary within wide limits. The stabiliser is generally used in a quantity of from 0.001 to 1 mol and preferably in a quantity of from 0.1 to 0.5 mol per mol of hydrogen peroxide. The reaction temperature applied in the process according to the invention is in the range from 20° to 150° C and preferably in the range from 30° to 100° C. The pressure is not critical to the reaction. In principle, the reaction may even be carried out under excess pressure or in vacuo. The reaction components may be completely or partly in the gas phase. In order to dissipate the heat of reaction, the reaction vessel may be cooled with a suitable medium. In order to adjust the exact reaction temperature required, the pressure prevailing in the reaction vessel is best selected so that the reaction mixture just boils.

The reaction time is governed by the type of phenol or phenol ether to be hydroxylated, but also by temperature, by the molar ratio and concentration of the reactants, by the type of solvent and by the type, quantity and concentration of the acid. The velocity of the reaction is at its highest where the reaction is carried out with a high acid concentration in the absence of a solvent. In general, the reaction conditions are selected so that the reaction takes place at such a velocity that more than 99% of the hydrogen peroxide has reacted after 0.5 to 3 hours and preferably after 1 to 2 hours.

The reaction mixture may be worked up for example by neutralising the acid and subjecting the reaction mixture to fractional distillation in vacuo. Insoluble constituents of the reaction mixture, for example fluorinated or sulphonated resins, may be filtered off after the reaction. The reaction mixture may also be worked up by extraction or by a combination of extraction and distillation processes.

The phenol or phenol ether used in excess may be reused for the reaction, optionally after purification.

In general, two isomeric hydroxyl derivatives of the starting compounds are formed from the phenols or phenol ethers in the process according to the invention. In the case of mononuclear, unsubstituted phenol ethers, o- and p-hydroxylated products are almost exclusively formed. For example, o- and p-hydroxy anisole are formed from anisole, whilst o- and p-hydroxy phenyl ethyl ether are formed from phenyl ethyl ether. In the case of substituted phenols or phenol ethers, more than two isomers may possibly be formed, although the o-hydroxylated end product generally predominates. In the case of phenols or phenol ethers derived from naphthalene, anthracene or phenanthrene, a larger number of isomers is generally formed than in the case of benzene derivatives. Thus, 1,2-dihydroxy napthalene and 2,4-dihydroxy naphthalene, together with a little 2,6-dihydroxy naphthalene, are formed for example in the hydroxylation of β-naphthol.

EXAMPLE 1 a. Preparation of an anhydrous solution of hydrogen peroxide in p-cresol 480 g of p-cresol were introduced into a distillation apparatus fitted with a 50 cm long Vigreux column having a thermostatically controlled condenser and receiver. The p-cresol was then distilled off at 6 Torr with a reflux ratio of 1:1, the temperature at the head of the Vigreux column being 72° C. The temperature in the sump of the distillation apparatus was between 75° C and 76° C. After the distillation rate had become constant under these conditions (16 g of p-cresol in 15 minutes), the p-cresol which had collected in the receiver was run off, and 27.5 g of a 7.65% anhydrous solution of hydrogen peroxide in triisooctyl phosphate were introduced into the column over a period of 40 minutes from a dropping funnel. After the 40 minutes, 44.7 g of a 4.7% anhydrous solution of hydrogen peroxide in p-cresol were removed from the receiver set thermostatically at 42° C.

b. Hydroxylation of p-cresol 40.2 g of an anhydrous 4.7% solution of hydrogen peroxide in p-cresol (= 55.6 mMol of hydrogen peroxide) heated to 45° C were added dropwise over a period of 15 minutes at 60° C to a stirred mixture of 50.7 g (0.469 mol) of p-cresol and 1.36 g (13.9 mMol) of 100% sulphuric acid. The reaction temperature was kept at 70° C. After the hydrogen peroxide solution had been added dropwise, the reaction mixture was stirred for 30 minutes at 70° C.

By this time 94.6% of the hydrogen peroxide had reacted. The yield of 4-methyl pyrocatechol amounted to 4.28 g (34.5 mMol), and the yield of 4-methyl resorcinol to 0.535 g (4.3 mMol). The total yield of both diphenols, based on the hydrogen peroxide reacted, was 73.8%.

EXAMPLE 2

25 g of an anhydrous 15.8% solution of hydrogen peroxide in methanophosphonic acid dimethyl ester (= 3.95 g of hydrogen peroxide = 116 mMol) were added dropwise over a period of 15 minutes to a stirred mixture of 232.3 g (2.15 mol) of p-cresol and 2.1 g (21.4 mMol) of 100% sulphuric acid heated to 50° C. After the hydrogen peroxide solution had been added, the reaction mixture was stirred for 55 minutes at 75° C in order to complete the reaction.

The reaction mixture was found to contain 9.84 g (79.4 mMol) of 4-methyl pyrocatechol and 1.03 g (8.3 mMol) of 4-methyl resorcinol. The total yield of both diphenols, based on the hydrogen peroxide use, was 75.6%.

EXAMPLE 3

84.7 g (0.784 mol) of p-cresol were introduced with stirring at 45° C into 21.5 g of an anhydrous 8.32% solution of hydrogen peroxide in triisooctyl phosphate. This was followed by the addition of 1.5 g (15 mMol) of fluorosulphonic acid, after which the temperature of the mixture rose to 93° C. After the reaction had abated, the reaction mixture was stirred for 45 minutes at 70° C. Thereafter it was not possible to detect any more hydrogen peroxide in the reaction mixture.

The reaction mixture was found to contain 4.45 g (35.85 mMol) of 4-methyl pyrocatechol and 0.535 g (4.31 mMol) of 4-methyl resorcinol. The total yield of diphenols was to 76.3%, based on the hydrogen peroxide used. The selectivity for 4-methyl resorcinol was 8.2%.

EXAMPLE 4

An anhydrous solution of 19.7% of hydrogen peroxide in methanophosphonic acid dimethyl ester (1.36 g of hydrogen peroxide = 40 mMol) was added with stirring at 70° C to 120 g (0.8 mol) of p-tert.-butyl phenol in 35 g of methanophosphonic acid dimethyl ester. Following the addition of 1 g (10.2 mMol) of 100% sulphuric acid, the temperature rose to 76° C. 96.5% of the hydrogen peroxide had reacted after stirring for 1 hour at 70° C.

The reaction mixture was found to contain 5.68 g (34.2 mMol) of 4-tert.-butyl pyrocatechol. Based on the hydrogen peroxide reacted, this corresponded to a yield of 88.5%.

EXAMPLE 5

21.5 g of an anhydrous 8.32% solution of hydrogen peroxide in triisooctyl phosphate were added dropwise to a stirred mixture of 98 g (0.762 mol) of p-chlorophenol and 3 g (30 mMol) of fluorosulphonic acid heated to 60° C. The reaction mixture was stirred for 1 hour at 70° C to complete the reaction of the hydrogen peroxide.

The reaction mixture was found by gas chromatography to contain 5.22 g (36 mMol) of 4-chloropyrocatechol, corresponding to a yield of 68.4%, based on the hydrogen peroxide used.

EXAMPLE 6

139 g (0.816 mol) of 4-hydroxy biphenyl in 80 g of methanophosphonic acid dimethyl ester were added with stirring at 65° C to 2.45 g (25 mMol) of 100% sulphuric acid. 9.5 g of an anhydrous 21.5% solution of hydrogen peroxide in methanophosphonic acid dimethyl ester (2.04 g of hydrogen peroxide = 60 mMol) were then added dropwise over a period of 10 minutes. The reaction temperature was kept at 65° C. All the hydrogen peroxide had reacted after 45 minutes.

The reaction mixture was found by gas chromatographic analysis to contain 6.24 g (33.5 mMol) of 4-phenyl pyrocatechol. Based on the hydrogen peroxide used, this corresponded to a yield of 55.8%.

EXAMPLE 7 a. Preparation of an anhydrous solution of hydrogen peroxide in anisole.

520 ml of anisole were introduced into a distillation apparatus equipped with a 50 cm long Vigreux column having a thermostatically controlled condenser and receiver. The anisole was then distilled off at 45 Torr with a reflux ratio of 1:1, the temperature at the head of the Vigreux column being 73° C. The temperature prevailing in the sump of the distillation apparatus was between 76° C and 77° C. After the distillation rate had become constant under these conditions (2.2 ml of anisole in 1 minute), the anisole which had collected in the receiver was run off, and 46 g of a 4.2% anhydrous solution of hydrogen peroxide in triisooctyl phosphate were introduced into the column over a period of 50 minutes from a dropping funnel. After 52 minutes, 110.5 g of a 1.71% anhydrous solution of hydrogen peroxide in anisole were removed.

b. Hydroxylation of anisole.

100 g of an anhydrous 1.71% solution of hydrogen peroxide in anisole (1.71 g of hydrogen peroxide = 50.3 mMol) were added dropwise over a period of 15 minutes to a stirred mixture of 55 g of methanophosphonic acid dimethyl ester and 1.2 g (12.25 mMol) of 100% sulphuric acid. After the peroxide-containing solution had been added, the reaction mixture was heated for 1 hour to 85° C. Thereafter no more hydrogen peroxide could be detected.

The reaction mixture was found to contain 3.14 g (25.3 mMol) of guaiacol and 0.906 g (7.3 mMol) of hydroquinone monomethyl ether. The total yield of both phenols amounted to 64.8%, based on the hydrogen peroxide used.

EXAMPLE 8

6.6 g of an anhydrous 17.8% solution of hydrogen peroxide in methanophosphonic acid dimethyl ester (1.175 g of hydrogen peroxide = 34.5 mMol) were added dropwise at 60° C to a stirred mixture of 54 g (0.5 mol) of anisole in 20 ml of methanophosphonic acid dimethyl ester and 1.6 g (16.3 mMol) of 100% sulphuric acid. The reaction mixture was then heated for 55 minutes to 85° C by this time 97.6% of the hydrogen peroxide had reacted.

The reaction mixture was found to contain 2.14 g (17.25 mMol) of guaiacol and 0.813 g (6.55 mMol) of hydroquinone monomethyl ether. Based on the hydrogen peroxide reacted, this corresponds to a total yield of methoxy phenols of 70.6%.

EXAMPLE 9

7.3 g of an anhydrous 15.5% solution of hydrogen peroxide in methanophosphonic acid dimethyl ester (1.13 g of hydrogen peroxide = 33.2 mMol) were added to a stirred mixture, heated to 60° C, of 60 g (0.491 mol) of p-cresol methyl ether, 20 g of methanophosphonic acid dimethyl ester and 1.6 g (16.3 mMol) of 100% sulphuric acid. After the reaction mixture had been stirred for 1 hour at 85° C, all the hydrogen peroxide had reacted.

The reaction mixture was found by gas chromatography to contain 3.09 g (22.4 mMol) of 2-methoxy-5-methyl phenol. Based on the hydrogen peroxide used, this corresponded to a yield of 67.5%.

What we claim is:

1. In a catalytic process for the hydroxylation of the nucleus of a phenol or phenol ether wherein a phenol or phenol ether is contacted with hydrogen peroxide at a temperature of 20°-150° C and at a pressure of 0.1 to 500 Torr employing 3 to 20 moles of said phenol or phenol ether per mole of hydrogen peroxide and the resulting hydroxylated phenol or phenol ether is recovered, the improvement which comprises employing a substantially anhydrous hydrogen peroxide obtained by distilling off said hydrogen peroxide together with the phenol or phenol ether to be hydroxylated from a nonaqueous solution whose solvent boils at a temperature higher than said phenol or phenol ether to be hydroxylated and affecting the hydroxylation in the presence of a strong acid either before or after condensing the vapor mixture which forms during the said distillation.

2. A process as claimed in claim 1, wherein at least one stabiliser is used in conjunction with the hydrogen peroxide.

3. A process as claimed in claim 1, wherein an ester or N-alkyl amide of phosphoric acid, phosphonic acid or phosphinic acid is used as the higher boiling solvent for hydrogen peroxide.

4. A process as claimed in claim 1, wherein from 10 to 15 mols of the phenol or phenol ether are used per mol of hydrogen peroxide.

5. A process as claimed in claim 1, wherein the strong acid is sulphuric acid, sulphuric acid in admixture with phosphoric acid, a fluorine-substituted polymeric sulphonic acid, fluorosulphonic acid, a perfluorinated alkyl sulphonic acids or fluorosulphonic acid in admixture with antimony pentafluoride.

6. A process as claimed in claim 1, wherein from 0.01 to 2.0 mols of the strong acid is present in reaction mixture per mol of hydrogen peroxide.

7. A process as claimed in claim 6, wherein from 0.1 to 1.5 mols of the strong acid is present in reaction mixture per mol of hydrogen peroxide.

8. A process as claimed in claim 1, wherein the reaction is carried out in the presence of a stabiliser in a quantity of from 0.001 to 1 mol per mol of hydrogen peroxide.

9. A process as claimed in claim 8, wherein the reaction is carried out in the presence of 0.1 to 0.5 mol of stabiliser per mol of hydrogen peroxide.

10. A process as claimed in claim 8 wherein the stabiliser is an ester or an N-alkyl amide of phosphoric acid, phosphonic acid or phosphinic acid.

11. A process as claimed in claim 1, wherein the reaction is carried out at a temperature in the range of from 30° C to 100° C.

12. A process as claimed in claim 1, wherein the reaction is carried out continuously with recycling of the unreacted reactants.

13. A process according to claim 1, wherein the solvent of said hydrogen peroxide is selected from the group consisting of tri-n-butyl phosphate, tri-n-octyl phosphate, tri-[(2-ethyl)-hexyl]-phosphate, hexamethyl phosphoric acid triamide, β-carbomethoxy ethanophosphonic acid methyl ester and β-carbohydroxy ethanophosphonic acid methyl ester.

14. A process according to claim 13 wherein a 5–30% solution of hydrogen peroxide in an anhydrous organic solvent is used.

15. A process according to claim 14 wherein a 10–25% solution of hydrogen peroxide in an anhydrous organic solvent is used.

16. A process according to claim 1 wherein vapors of distilled off hydrogen peroxide are introduced into an anhydrous solvent thereof thereby forming an anhydrous hydrogen peroxide solution and to said anhydrous hydrogen peroxide solution there is added said phenol or phenol ether and said phenol or phenol ether is reacted therein with said hydrogen peroxide in the presence of said strong acid at said temperature and pressure.

17. A process according to claim 16 wherein vapors of said phenol or phenol ether are added to said hydrogen peroxide solution so formed.

18. A process according to claim 16 wherein said solvent into which said hydrogen peroxide is introduced is a phenol or phenol ether.

19. A process according to claim 1 wherein hydrogen peroxide is distilled over from a solution together with a phenol or phenol ether and is reacted with said phenol or phenol ether in the presence of a strong acid while said phenol or phenol ether is in the liquid phase.

20. A process according to claim 1 wherein said hydrogen peroxide is distilled over together with phenol or phenol ether and is reacted with said phenol or phenol ether in the presence of said strong acid while said phenol or phenol ether is in the vapor phase.

* * * * *